United States Patent [19]

Guy

[11] Patent Number: 5,576,311
[45] Date of Patent: Nov. 19, 1996

[54] CYCLODEXTRINS AS SUSPENDING AGENTS FOR PHARMACEUTICAL SUSPENSIONS

[75] Inventor: Yaacov J. Guy, Rehovot, Israel

[73] Assignee: Pharmos Corporation, New York, N.Y.

[21] Appl. No.: 346,954

[22] Filed: Nov. 30, 1994

[51] Int. Cl.[6] .......................... A61K 31/56; A61K 47/00
[52] U.S. Cl. ........................ 514/179; 514/777; 514/914
[58] Field of Search ................................. 514/179, 777, 514/914

[56] References Cited

U.S. PATENT DOCUMENTS

| | | | |
|---|---|---|---|
| 2,861,920 | 11/1958 | Dale et al. | 167/65 |
| 4,383,992 | 5/1983 | Lipari | 424/238 |
| 4,596,795 | 6/1986 | Pitha | 514/58 |
| 4,710,495 | 12/1987 | Bodor | 514/174 |
| 4,727,064 | 2/1988 | Pitha | 514/58 |
| 5,089,482 | 2/1992 | Hermans et al. | 514/58 |

FOREIGN PATENT DOCUMENTS 1222697  6/1987  Canada.

OTHER PUBLICATIONS

CA 117:178175, Alberth et al., 1991.
Remington's Pharmaceutical Sciences, 18th Ed., pp. 1587–1592, 1990.

*Primary Examiner*—Kimberly Jordan
*Attorney, Agent, or Firm*—Pennie & Edmonds

[57] ABSTRACT

The present invention relates to stable aqueous suspension of drugs suitable for therapeutic administration without requiring solubilization or complexation of those drugs. The suspensions are stabilized with cyclodextrin type suspending agents. Stabilized suspensions of corticosteroids which employ these suspending agents are useful for therapeutic treatment of the eye, ear, or nose.

25 Claims, No Drawings

5,576,311

CYCLODEXTRINS AS SUSPENDING AGENTS FOR PHARMACEUTICAL SUSPENSIONS

FIELD OF INVENTION

The invention relates to stable aqueous suspensions of poorly water soluble drugs for treatment of ophthalmic and otolaryngological inflammations or any other conditions requiring use of a drug in a suspension.

BACKGROUND OF THE INVENTION

Numerous drugs are prepared in the form of suspensions for ophthalmic, oral, otic, nasal and respiratory topical applications. Formulation of pharmaceutical dosages of water-insoluble drugs as suspensions is frequently hampered by the subsequent formation of cakes resulting from aggregation of the suspended material. Polymeric compounds (e.g. polyvinyl pyrrolidone ("PVP"), polyvinyl alcohol ("PVA"), and dextran are commonly used to stabilize such suspensions. An alternative approach to the preparation of such drugs is to enhance the solubility of the drugs within the formulation by vehicles such as emulsions, liposomes, and cyclodextrins. However, certain drugs, in their therapeutic concentrations, are not sufficiently stabilized or solubilized by these methods for the above-mentioned applications.

Generally, a variety of cyclodextrins have been used to solubilize poorly water-soluble or water-insoluble drugs and to stabilize drugs which are unstable in water in the form of inclusion complexes. The present invention relates to the entirely novel use of modified cyclodextrins to stabilize and facilitate the formation of aqueous suspensions of particulate water-insoluble drugs.

Cyclodextrins are cyclic oligosaccharides. The most common cyclodextrins are α-cyclodextrin, which is composed of a ring of six glucose residues; β-cyclodextrin, which is composed of a ring of seven glucose residues; and γ-cyclodextrin, which is composed of a ring of eight glucose units. The inside cavity of a cyclodextrin is lipophilic, while the outside of the cyclodextrin is hydrophilic; this combination of properties has led to widespread study of natural cyclodextrins, particularly in connection with pharmaceuticals, and many inclusion complexes have been reported. β-Cyclodextrin has been of special interest because of its cavity size, but its relatively low aqueous solubility (about 1.8% w/v at 25° C.) and attendant nephrotoxicity have limited its use in the pharmaceutical field.

Attempts to modify the properties of natural cyclodextrins have resulted in the development of heptakis (2,6-di-O-methyl)-β-cyclodextrin, heptakis (2,3,6-tri-O-methyl)-β-cyclodextrin, hydroxypropyl-β-cyclodextrin, β-cyclodextrin-epichlorohydrin polymer and others. For a comprehensive review of cyclodextrins and their use in pharmaceutical research, see Pitha et al, in *Controlled Drug Delivery*, ed. S. D. Bruck, Vol. I, CRC Press, Boca Raton, Fla., pp. 125–148 (1983). For an even more recent overview, see Uekama et al, in *CRC Critical Reviews in Therapeutic Drug Carrier Systems*, Vol. 3(1), 1–40 (1987); Uekama, in *Topics in Pharmaceutical Sciences* 1987; Uekama, in *Topics in Pharmaceutical Sciences* 1987, eds. D. D. Breimer and P. Speiser, Elsevier Science Publishers B. V. (Biomedical Division), 1987, 181–194 and Pagington, *Chemistry in Britain* May 1987; pp. 455–458.

Inclusion complexes of α-, β- or γ-cyclodextrin or their mixtures with a variety of drugs have been described by numerous parties and various advantages have been attributed to the complexes. See U.S. Pat. Nos. 4,024,223; 4,228,160; 4,232,009; 4,351,846; 4,352,793; 4,383,992; 4,407,795; and 4,424,209.

Topical steroids such as corticosteroids are commonly used for anti-inflammatory therapy of the eye, especially for treating inflammatory conditions of the palpebral or bulbar conjunctiva, cornea and anterior segment of the globe. Common therapeutic applications for steroids include allergic-conjunctivitis, acne rosacea, superficial punctate keratitis and iritis cyclitis. Steroids also are used to ameliorate inflammation associated with corneal injury due to, chemical or thermal burns, or penetration of foreign bodies. Such conditions may result from surgery, injury, allergy or infection to the eye and can cause severe discomfort.

Despite their therapeutic advantages, topical ocular use of corticosteroids is associated with a number of complications, including posterior subcapsular cataract formation, elevation of intraocular pressure, secondary ocular infection, retardation of corneal wound healing, uveitis, mydriasis, transient ocular discomfort and ptosis. Numerous systemic complications also may arise from the topical ocular application of corticosteroids. These complications include adrenal insufficiency, Cushing's syndrome, peptic ulceration, osteoporosis, hypertension, muscle weakness or atrophy, inhibition of growth, diabetes, activation of infection, mood changes and delayed wound healing.

Topical steroids for treating ocular inflammations can be based on soft drugs. Soft drugs, as are known in the art, are designed to provide maximal therapeutic effect and minimal side effects. By one approach, synthesis of a "soft drug" can be achieved by structurally modifying a known inactive metabolite of a known active drug to produce an active metabolite that undergoes a predictable one-step transformation in-vivo back to the inactive metabolite. (See U.S. Pat. Nos. 4,996,335 and 4,710,495 for "soft" steroids). "Soft drugs" therefore are biologically active chemical components characterized by predictable in vivo metabolism to non-toxic derivatives after they provide their therapeutic effect.

Pharmaceutical compositions of water-insoluble drugs such as corticosteroids in aqueous suspensions for ocular and other uses must satisfy constraints imposed by physiological compatibilities such as pH, osmolality, and particle size of the suspended steroids. Furthermore, these compositions must meet requirements for preservative efficiency and ease of suspension over extended periods of time.

Therapeutic suspensions of corticosteroids typically employ polymeric compounds such as PVP and PVA as suspending agents in concentrations ranging from 0.1 to 10%. See U.S. Pat. No. 2,861,920. Polymeric compounds such as PVP, PVA, sodium carboxymethylcellulose, dextran, and surface-active agents such as Polysorbate 80, Polysorbate 20, and tyloxapol also have been used to stabilize corticosteroid suspensions intended for ophthalmic, nasal, and otic uses.

The amounts of polymeric compounds and surface active agents employed to provide stability to these suspensions must accurately be determined. For example, an excessive amount of polymeric compound may hamper the antimicrobial effects of preservatives added to the suspension. Also, pharmaceutical ocular and nasal dosages of these suspensions either must be buffered or have a pH with no buffering capacity. These suspensions also should be isotonic.

Formulation of aqueous suspensions of corticosteroids for ocular applications and other uses has been hampered by agglomeration of the steroid particles. Agglomeration particularly has been a problem for "soft" steroids such as loteprednol etabonate ("LE"), bechmethasone, betamethasone, fluocinolone, fluoromethalone, prednisolone, either alone or in combination with other therapeutic drugs such as betaxalol, athenolol, livobanolol, epinenephrin, dipivalyl, oxonolol, acetazilumide-base, methazalomide, tobramycin, gentamycin, piroxicam, indomethacine, naproxen, phenylbutazone, ibuprofen, diclofenac-acid.

LE is a soft corticoseroid that has ocular anti-inflammatory activity. This corticosteroid is based on a known inactive metabolite of the active drug prednisolone. LE is an analog of prednisolone that does not have a 20-keto group attached to the 17β-position. Instead, the 17-β position is occupied with a metabolically-labile ester function. In biological systems, LE is hydrolysed to the inactive carboxylic acid metabolite (PJ-91) that does not bind to glucocorticoid receptors. LE also provides superior safety by reducing the risk of steroid induced cataracts and elevation of intra-ocular pressure. The lability of LE to enzymes located in the blood and/or liver also reduces the likelihood of systemic side effects.

Soft steroids such as corticosteroids have the potential for treating inflammation without inducing elevation of intraocular pressure. In addition, these steroids lessen the tendency to induce cataracts which may result from interaction of the corticosteroids with the ocular lens proteins.

LE provides therapeutic advantages over other corticosteroids by providing efficacy similar to its parent compound, namely, prednisolone acetate. Stable aqueous suspensions of LE, however, cannot be obtained by accepted buffering systems or ionic tonicity agents. Surprisingly, common tonicity agents such as aqueous solutions containing 0.9% NaCl, 10% EDTA, or phosphate buffer, even in concentrations as low as 1 mM therefore can not be employed in aqueous suspensions of corticosteroids such as LE.

A need therefore exists for aqueous suspensions which have therapeutically effective amounts of "soft" drugs such as corticosteroids, but which avoid the problems of agglomeration associated with the suspensions of the prior art.

SUMMARY OF THE INVENTION

New suspensions of water insoluble or poorly soluble drugs are now provided. These suspensions include component (A) of a therapeutic concentration of a water insoluble or poorly soluble drug of particles less than ten microns, and component (B) of an amorphous cyclodextrin in an aqueous medium, wherein the molar ratio of component (A) to component (B) is about 1:0.5 to 1:20, preferably, about 1:0.5 to 1:6.

Component (A) may be a therapeutic quantity of a nonsteroidal antiinflammatory drug such as indomethacin in a concentration of about 0.1 to 3% (w/w); a therapeutic quantity of an antimicotic such as miconazole in a concentration of about 0.1 to 2% (w/w); a therapeutic quantity of an antiepileptic such as phenytoin in a concentration of about 0.1 to 4% (w/w); a therapeutic quantity of an antihistamine such as mebhydroline in a concentration of about 0.5 to 5% (w/w); or a therapeutic quantity of an antihistamine such as mebhydroline. Component (A) also may be a therapeutic quantity of a locally active steroid, such as LE, bechmethasone, betamethasone, fluocinolone, fluoromethalone, prednisolone, preferably LE, in a concentration of 0.1 to 10% (w/w), preferably 0.5 to 5% of the suspension.

Component (B) can be an amorphous cyclodextrin such as hydroxypropyl cyclodextrin ("HPCD"), beta cyclodextrin ("BCD"), and hydroxyethyl cyclodextrin ("HECD"), preferably HPCD. The cyclodextrins of component (B) surprisingly can be used as effective suspending agents to maintain suspensions of water-insoluble drugs which average $\leq 10$ μm particle size for ophthalmic or enteral use.

In another aspect of the invention, aqueous suspensions for ophthalmic, otolaryngological, or anti-inflammatory use which comprise the aforementioned component (A) and the aforementioned component (B) in an aqueous medium, further may be combined with component (C) of a nonionic surface active agent.

The suspensions of the invention further may include component (D) of a tonicity imparting agent to impart isotonicity, and component (E) of at least one preservative compound to substantially prevent microbial growth. Preferably, component (D) is glycerol in an amount of about 2 to 2.8% by weight of the suspension.

The invention also provides stable aqueous suspensions of water-insoluble drugs which can remain in such a state that will allow for immediate suspension of the drugs when desired, even after extended periods of settling or standing. Suspensions of drugs which employ these suspending agents, moreover, do not cause discomfort upon application. Moreover, in the suspensions of the invention, surprisingly less than 2% of component (A) is solubilized by component (B). As used herein, stable suspensions are those which maintain the particles in a suspended state for a minimum of one year, typically about two to three years.

In a preferred aspect, stable aqueous suspensions of LE, i.e., suspensions which are stable for at least one year, typically 2–3 years, are provided which have concentrations of about 0.5–1% of LE with a cyclodextrin, preferably HPCD, and a surface active agent of tyloxapol. Accepted preservatives such as benzalkonium chloride and disodium edentate ("EDTA") can be included in the suspension. Although surface active agents may be employed, use of cyclodextrins as suspending agents surprisingly provide sufficient stability to the suspensions to minimize use of surface active agents which may neutralize the effects of preservatives. In such suspensions, less than about 5% of cyclodextrins are used to suspend the drug in a stable manner.

Having briefly summarized the invention, the invention will now be described in detail by reference to the following specification and non-limiting examples. Unless otherwise specified, all percentages are by weight and all temperatures are in degrees Celsius.

DETAILED DESCRIPTION OF THE INVENTION

Therapeutic, aqueous suspensions of a drug of component (A) for ophthalmic or otolaryngological use are made by aseptic preparation. The suspensions of the invention are prepared by mixing the drug of component (A), a suspending agent of component (B), and an aqueous medium, preferably purified water. Optionally, component (C) of a surface-active agent, component (D) of an agent for producing isotonicity, and component (E) of preservative(s) may be included in the aqueous medium. Purity levels of all materials employed in the suspensions of the invention exceed 98%.

Component (A) typically is added to obtain a final concentration in the suspension of about 0.1–10%, preferably about 0.5–5%, most preferably about 0.1%–2% based on the weight of the suspension. The molar ratio of component (A) to component (B) typically is in the range of 4:1–1:100, preferably about 2:1 to 1:20, more preferably about 2:1 to 1:6.

Component (B) is a cyclodextrin such as methyl cyclodextrin, glucosyl cyclodextrin, maltosyl cyclodextrin, multiple derivative forms of the above cyclodextrins, BCD, and HECD, particularly HPCD.

Component (C) is a surface-active agent that is acceptable for ophthalmic or otolaryngological uses. Useful surface active agents include but are not limited to non-ionic surfactants such as Polysorbate 80 from ICI Americas, Wilmington, Del., Polysorbate 20 from ICI Americas, Wilmington, Del. and Tyloxapol from ICI Americas, Wilmington, Del. The concentration in which the surface active agent may be used is only limited by neutralization of the bacteriocidal effects of the accompanying preservatives employed, or by concentrations which may cause irritation.

Component (D) can be a diol such as glycerol in a concentration of about 2–2.8%, preferably about 2.2–2.6% based on the weight of the suspension in order to provide isotonicity.

The suspension thus can be prepared (hereinafter referred to as "Method 1") by thoroughly mixing the drug (component A) and the indicated suspending agent (component B) with the indicated surface active agent (component C), glycerol for tonicity adjustment, and preservatives, in an aqueous medium.

The cyclodextrins of component (B) and the surface active agents of component (C) have good solubility in water, have sufficient number of hydroxyl groups to interact with the drug, and have mild effects on the viscosity of the suspension.

Health regulations in various countries generally require that ophthalmic preparations shall include a preservative. Many well known preservatives that have been used in ophthalmic preparations of the prior art, however, cannot be used in the preparations of the invention since those preservatives may no longer be considered safe for ocular use or may interact with the surfactant employed in the suspension to form a complex that reduces the bacteriocidic activity of the preservative.

The preservatives of component (E) employed in the suspensions of the invention are chosen to avoid interacting with the surface active agent to an extent that the preservatives are prevented from protecting the suspension from microbiological contamination. The preservative(s), when required, are employed in a minimal concentration sufficient to prevent microbial growth.

A variety of preservatives may be employed in the suspensions of the invention. In a preferred embodiment, benzalkonium chloride may be employed as a safe preservative. Other possible preservatives include but are not limited to benzyl alcohol, methyl parabens, propyl parabens, benzethonium chlorides, thimerosal (concentration of 0.01–0.2%) and chlorbutanol (concentration of 0.01–0.2%). Preferably, a preservative (or combination of preservatives) which imparts standard antimicrobial activity to the suspension and which protects against oxidation of components (A)–(D) is employed. The preservative typically can be added to attain a concentration of 0.001–0.02% preferably 0.005–0.015%, based on the weight of the suspension.

Additional therapeutic drugs such as drugs for treating glaucoma, anti-inflammatory drugs, antibiotic drugs, anti-cancer drugs, anti-fungal drugs and anti-viral drugs may be included in the suspensions of the invention. Examples of anti-glaucoma drugs include but are not limited to timolol-base, betaxalol, athenolol, livobanolol, epinenephrin, dipivalyl, oxonolol, acetazilumide-base and methazalomide. Examples of anti-inflammatory drugs include but are not limited to steroids such as cortisone and dexamethasone, and non-steroids such as piroxicam, indomethacine, naproxen, phenylbutazone, ibuprofen and diclofenac-acid. Additional therapeutic materials which may be employed include but are not limited to tobromycin.

The drugs of component (A) typically have particle sizes of about 0.1 µm–30 µm, preferably 0.8–10µ, most preferably about 2–5µ in diameter. Drugs such as LE in this size range are commercially available from suppliers such as the Sipsy Co., Arville, France.

Stable aqueous suspensions of the invention can be produced over a broad range of pH values. A pH of about 3–9, preferably about 4–8, most preferably about 4.5–7.5 is useful for preparing stable LE suspensions which employ cyclodextrins. A broad range of percents by weight of the cyclodextrin suspending agents and percents by weight of surface active agents can be employed to provide stable suspensions in accordance with the invention. Useful molar ratios of LE: cyclodextrin suspending agent can vary between about 4:1–1:100, preferably about 2:1 to 1:10.

Generally, method 1 is used to prepare the aqueous suspensions of Example 1–7. These suspensions are prepared by mixing the micronized soft drug of component (A), the cyclodextrin suspending agent of component (B), and the surface active agent of component(C). A tonicity agent of component (D) such as glycerol is added for tonicity adjustment and component (D) of preservatives such as benzalkonium and EDTA also may be employed.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In Examples 1–7, the compositions thereof are produced with the indicated percentages of the components given in Table 1 using the above-described Method 1.

TABLE 1

| Example | % Drug | % Dextrin | % Tyloxapol | % Glycerol | % EDTA | % Benzalkonium chloride | Purified $H_2O$ |
| --- | --- | --- | --- | --- | --- | --- | --- |
| 1A | 0.5 LE[1] | 0.5 HPCD | 0.3 | 2.4 | 0.01 | 0.01 | Remainder |
| 1B | 1.0 LE | 1.0 HPCD | 0.3 | 2.4 | 0.01 | 0.01 | " |
| 1C | 0.5 LE | 1.0 HPCD | 0.3 | 2.4 | 0.01 | 0.01 | " |
| 1D | 1.0 LE | 1.0 HPCD | 0.3 | 2.4 | 0.01 | 0.01 | " |
| 2A | 0.5 LE | 1.0 BCD | 0.3 | 2.4 | 0.01 | 0.01 | " |
| 2B | 1.0 LE | 1.0 BCD | 0.3 | 2.4 | 0.01 | 0.01 | " |

TABLE 1-continued

| Example | % Drug | % Dextrin | % Tyloxapol | % Glycerol | % EDTA | % Benzalkonium chloride | Purified H$_2$O |
|---|---|---|---|---|---|---|---|
| 3A | 0.5 LE | 1.0 HECD | 0.3 | 2.4 | 0.01 | 0.01 | " |
| 3B | 1.0 LE | 1.0 HECD | 0.3 | 2.4 | 0.01 | 0.01 | " |
| 4A | 1.0 ID[2] | 0.5 HPCD | 0.3 | 2.4 | 0.01 | 0.01 | " |
| 4B | 1.0 ID | 1.0 HPCD | 0.3 | 2.4 | 0.01 | 0.01 | " |
| 5A | 2.0 MI[3] | 0.5 HPCD | 0.3 | 2.4 | 0.01 | 0.01 | " |
| 5B | 2.0 MI | 1.0 HPCD | 0.3 | 2.4 | 0.01 | 0.01 | " |
| 6A | 0.5 PH[4] | 0.5 HPCD | 0.3 | 2.4 | 0.01 | 0.01 | " |
| 6B | 0.5 PH | 1.0 HPCD | 0.3 | 2.4 | 0.01 | 0.01 | " |
| 7 | 5.0 ME[5] | 0.05 HPCD | 0.03 | 2.4 | 0.01 | 0.01 | " |

[1]LOTEPREDNOL ETABONATE
[2]INDOMETHACIN
[3]MICHANAZOLE
[4]PHENYTOIN
[5]MEBHYDROLIN

Evaluation of Particle Stability Over Time

Samples of suspensions of corticosteroids that have an average size of $\leq 10$ μm are tested for stability using accelerated stability tests and "real time" studies.

The ability of cyclodextrins to provide stable suspensions of drugs such as LE is evaluated by three methods. The first method ("Method A") entails measuring the particle sizes with a Coulter LS130 instrument. When a drug such as LE is micronized to particle sizes of less than ten microns, an indication of suspension stability is that large agglomerates do not form, i.e., particle sizes averaging less than 10 μm are maintained. This is indeed observed in suspensions of LE that employ cyclodextrins.

A second approach ("Method B") for evaluating stability of suspensions of drugs such as LE is to centrifuge samples of those suspensions for two minutes at 5000 G to provide a pellet of the drug. The time required to suspend the resulting pellet by shaking provides a measure of stability. The results obtained by Method B indicate that >30 seconds of shaking required to suspend some sedimented particles, commercially available suspensions of fluorometholone and mebhydroline, when treated in this fashion. However, in the presence of cyclodextrins, suspensions of particles of fluorometholone and mebhydroline settled in this manner surprisingly are easily obtained with about five seconds of wrist shaking.

A third approach ("Method C") for evaluating stability of suspensions of drugs such as LE is to permit the particles in the samples to settle naturally, and to count the number of inversions required to resuspend the particles. The results obtained by Method C appear in Table 2.

The results obtained by Method C indicate that surprisingly few inversions are required to resuspend settled suspension of particles of LE which include cyclodextrin suspending agent relative to commercial suspensions which may require more than 50 inversions to suspend the particles.

TABLE 2

STABILITY OF VARIOUS MEDICINAL SUSPENSIONS FORMULATED WITH CYCLODEXTRIN

| Composition of Example No.: | Drug | Drug conc. (%) | CD[1] | CD[1] (%) | # Inversions[2] | Months Tested[3] |
|---|---|---|---|---|---|---|
| 1A | LE | 0.5 | beta-HPCD | 0.5 | 21 | 9 |
| 1B | LE | 1.0 | beta-HPCD | 1.0 | 20 | 9 |
| 1C | LE | 1.0 | beta-HPCD | 0.5 | 38 | 9 |
| 1D | LE | 0.5 | beta-HPCD | 1.0 | 12 | 9 |
| 2A | LE[4] | 0.5 | beta-BCD | 1.0 | 11 | 8 |
| 2B | LE | 1.0 | beta-CD | 1.0 | 16 | 8 |
| 3A | LE | 0.5 | HECD | 1.0 | 21 | 8 |
| 3B | LE | 1.0 | HECD | 1.0 | 35 | 8 |
| 4A | IN[5] | 1.0 | beta-HPCD | 0.5 | 14 | 7 |
| 4B | IN | 1.0 | beta-HPCD | 1.0 | 11 | 7 |
| 5A | MI[6] | 2.0 | beta-HPCD | 0.5 | 10 | 7 |
| 5B | MI | 2.0 | beta-HPCD | 1.0 | 13 | 7 |
| 6 | PH[7] | 0.5 | beta-HPCD | 1.0 | 5 | 7 |
| 7 | ME[8] | 5.0 | beta-HPCD | 0.5 | 7 | 6 |

[1]Cyclodextrin.
[2]Number of gentle wrist inversions required to suspend material naturally settled within the first week of preparation.
[3]During the testing period, samples were inverted to verify reliability of the number of inversions required for suspension. All of the indicated suspensions were found to maintain the same ease of suspension over the testing period.

TABLE 2-continued

STABILITY OF VARIOUS MEDICINAL SUSPENSIONS FORMULATED WITH CYCLODEXTRIN

| Composition of Example No.: | Drug | Drug conc. (%) | CD[1] | CD[1] (%) | # Inversions[2] | Months Tested[3] |
|---|---|---|---|---|---|---|

[4]Loteprednol Etabonate.
[5]Indomethacin.
[6]Miconazole.
[7]Phenytoin.
[8]Mebhydrolin.

HPLC MEASUREMENT OF LE

To evaluate solubilization of drugs such as LE by cyclodextrins, LE is continuously mixed with cyclodextrins in various concentrations in water for one week at room temperature. Samples of the resulting suspensions and the soluble fractions of LE are analyzed by high pressure liquid chromatography ("HPLC") before and after centrifugation at 5000 G, respectively (hereinafter referred to as "Method D"). The concentrations of LE are calculated from the area under the curve of the LE peak using known techniques. The extent of solubilization of LE by cyclodextrins is shown in Table 3.

The results in Table 3 indicate that not more than 0.01 mg/ml LE is solubilized by cyclodextrins.

TABLE 3

SOLUBILIZATION OF LOTEPREDNOL IN CYCLODEXTRIN SOLUTIONS

| Cyclodextrin in Suspension | LE Solubilized (mg/ml)[1] |
|---|---|
| 0.5%HPCD | 0.007 |
| 1.0%HPCD | 0.005 |
| 1.0%HECD | 0.01 |
| 1.0% BCD | 0.01 |

[1]maximum solubilization possible is 10 mg/ml

Measurement of the concentration of LE in suspensions of the above-mentioned samples is done using the HPLC technique of Method C. The results are shown in Table 4. As indicated in Table 4, the concentration of LE in the suspension was not significantly altered. Cyclodextrins therefore stabilize suspensions of drugs such as LE while minimizing solubilizing the LE.

TABLE 4

HPLC MEASUREMENT OF LE IN CYCLODEXTRIN SUSPENSIONS

| [LE] on label (mg/ml) | CD[1] | CD % | storage temp. (C) | period of storage (mos) | measurement (%) of label |
|---|---|---|---|---|---|
| 5 | HPCD[2] | 0.5 | 23 | 5.0 | 101.12 |
| 10 | HPCD | 0.5 | 23 | 5.0 | 109.09 |
| 5 | HPCD | 1 | 23 | 0.5 | 94.3 |
| 10 | HPCD | 1 | 23 | 0.5 | 88.18 |
| 5 | HPCD | 1 | 37 | 2.0 | 104.04 |
| 5 | HPCD | 1 | 45 | 2.0 | 96.84 |
| 5 | HPCD | 1 | 23 | 5.0 | 115.45 |
| 10 | HPCD | 1 | 23 | 5.0 | 110.23 |
| 5 | BCD[3] | 1 | 23 | 4.0 | 106.78 |
| 10 | BCD | 1 | 23 | 4.0 | 105.7 |
| 5 | HECD[4] | 1 | 23 | 4.0 | 104.26 |
| 10 | HECD | 1 | 23 | 4.0 | 135.88 |

[1]Cyclodextrin
[2]Hydroxypropyl Cyclodextrin
[3]Beta Cyclodextrin
[4]Hydroxyethyl Cyclodextrin It will be understood that the claims are intended to cover all changes and modifications of the preferred embodiments of the invention herein for the purpose of illustration which do not constitute departures from the spirit and scope of the invention.

What is claimed is:

1. A stable suspension of a drug comprising:
   an aqueous medium,
   component (A) of a therapeutic concentration of a drug in a particulate form that does not appreciably dissolve in the aqueous medium, and
   component (B) of a suspension agent comprising an amorphous cyclodextrin
   wherein the drug is retained in suspension in the aqueous medium without forming a soluble inclusion complex with the cyclodextrin.

2. The suspension of claim 1 wherein the molar ratio of component (A) to component (B) is about 4:1 to 1:100.

3. The suspension of claim 2 wherein the molar ratio is about 2:1 to 1:20.

4. The suspension of claim 3 wherein the molar ratio is about 2:1 to 1:6.

5. The suspension of claim 1 wherein component (A) is a locally active "soft" steroid, and component (B) is selected from the group of hydroxypropyl cyclodextrin, beta cyclodextrin, and hydroxyethyl cyclodextrin.

6. The suspension of claim 5 wherein component (A) is loteprednol etabonate and component (B) is hydroxypropyl cyclodextrin.

7. The suspension of claim 1, wherein the concentration of component (A) is about 0.05 to 5% based on the weight of the solution.

8. The suspension of claim 7 wherein the drug is water-insoluble and the concentration of component (B) is about 0.05 to 5% based on the weight of the solution.

9. The suspension of claim 1 further comprising a tonicity imparting agent for achieving isotonicity.

10. The suspension of claim 1 further comprising at least one preservative compound to prevent microbial growth in the suspension.

11. The suspension of claim 1 wherein less than about 2% of component (A) is solubilized by component (B).

12. The suspension of claim 1 wherein the drug has a particle size of about 0.1 to 30 μm.

13. The suspension of claim 1 further comprising a surface active agent, wherein the suspension is able to maintain the drug particles in a suspended state for at least one year.

14. A composition for ophthalmic or otolaryngological anti-inflammatory use comprising a stable suspension of:
   an aqueous medium,
   a component (A) of corticosteroid in a particulate form that does not appreciably dissolve in the aqueous medium,
   a component (B) of a suspension agent comprising a cyclodextrin,
   wherein the molar ratio of (A):(B) is about 4:1 to 1:100 and the corticosteroid is retained in suspension in the aqueous medium without forming a water soluble inclusion complex with the cyclodextrin.

15. The composition of claim 14 further comprising a tonicity agent.

16. The composition of claim 15 wherein said tonicity agent is glycerol.

17. The composition of claim 14 further comprising a preservative for preventing microbial formation in said composition.

18. The composition of claim 17 wherein said preservative is selected from the group of benzalkonium chloride and disodium edentate.

19. The composition of claim 18 further comprising a nonionic surfactant.

20. The composition of claim 14 wherein the corticosteroid is loteprednol-etabonate.

21. The composition of claim 20 wherein said cyclodextrin is hydroxypropyl cyclodextrin.

22. The composition of claim 20 further comprising a surface active agent, wherein the suspension is able to maintain the corticosteroid particles in a suspended state for at least two years.

23. The composition of claim 22 wherein the concentration of component (B) is about 0.05 to 5% based on the weight of the solution.

24. The composition of claim 14 wherein said cyclodextrin is selected from the group of hydroxypropyl cyclodextrin, beta cyclodextrin, and hydroxyethyl cyclodextrin.

25. The composition of claim 14 wherein the corticosteroid has a particle size of about 0.1 to 30 μm.

\* \* \* \* \*